United States Patent [19]

Thottathil

[11] Patent Number: 4,885,364

[45] Date of Patent: Dec. 5, 1989

[54] RESOLUTION PROCESS FOR BENZAZEPINE INTERMEDIATES

[75] Inventor: John K. Thottathil, Lawrenceville, N.J.

[73] Assignee: E. R. Squibb & Sons, Inc., Princeton, N.J.

[21] Appl. No.: 275,493

[22] Filed: Nov. 23, 1988

[51] Int. Cl.⁴ .............................................. C07D 223/16
[52] U.S. Cl. .................................................... 540/523
[58] Field of Search ........................................ 540/523

[56] References Cited

U.S. PATENT DOCUMENTS 4,748,239  5/1988  Floyd et al. .

OTHER PUBLICATIONS

P. Newman, "Optical Resolution Procedures for Chemical Compounds", vol. 3, pp. 15, 112, 115, 120–122, 163, 175, 231 (1984).

Primary Examiner—Robert T. Bond
Attorney, Agent, or Firm—Theodore R. Furman, Jr.

[57] ABSTRACT

In accordance with the present invention an improved process for preparing resolved compounds of the formula

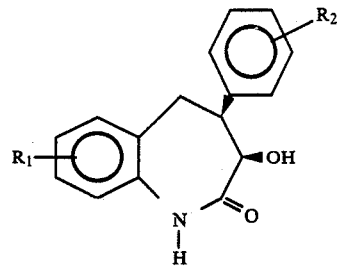

being the cis(+) isomer, is disclosed, wherein
$R_1$ and $R_2$ are each independently hydrogen, halogen, alkyl, alkoxy, aryloxy, arylalkoxy, diarylalkoxy, arylalkyl, cyano, hydroxy, alkanoyloxy,

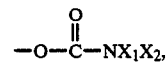

fluoro substituted alkoxy, fluoro substituted alkyl, (cycloalkyl)alkoxy —$NO_2$, $NX_3X_4$, —$S(O)_m$alkyl,

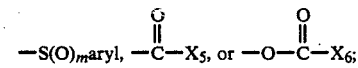

m is 0, 1 or 2;
$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;
$X_3$ and $X_4$ are each independently hydrogen, alkyl, alkanoyl, arylcarbonyl, heteroarylcarbonyl, or

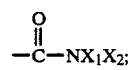

$X_5$ is hydroxy, alkoxy, aryloxy, amino, alkylamino or dialkylamino; and
$X_6$ is alkyl, alkoxy or aryloxy; with the proviso that if $R_4$ is a 7-alkyl group, it must have a tertiary carbon atom bonded to the ring.

19 Claims, No Drawings

RESOLUTION PROCESS FOR BENZAZEPINE INTERMEDIATES

BACKGROUND OF THE INVENTION

U.S. Pat. No. 4,748,239 to Floyd et al. discloses compounds having the general formula

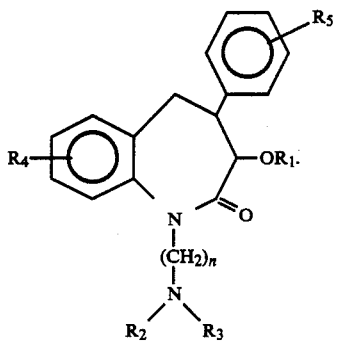

These compounds are vasodilators and therefore are especially useful as antihypertensive agents.

A key intermediate in the preparation of compounds of formula A and other such compounds, is the compound having the formula

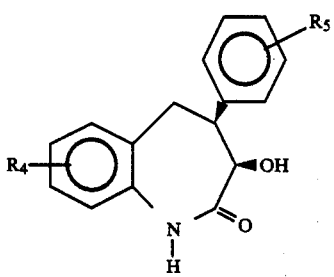

being the cis(+) isomer. This is so because the cis(+) isomers of compounds of formula A exhibit the greatest vasodilating activity. Several routes for providing the desired resolved products of formula A are outlined in the above-mentioned Floyd et al. patent.

SUMMARY OF THE INVENTION

In accordance with the present invention a new and improved process for preparing resolved compounds of the formula

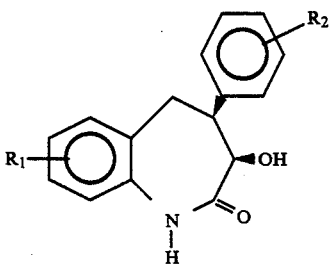

being the cis(+) isomer, is disclosed, wherein $R_1$ and $R_2$ are each independently hydrogen, halogen, alkyl, alkoxy, aryloxy, arylalkoxy, diarylalkoxy, arylalkyl, cyano, hydroxy, alkanoyloxy,

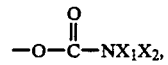

fluoro substituted alkoxy, fluoro substituted alkyl, (cycloalkyl)alkoxy, $-NO_2$, $NX_3X_4$, $-S(O)_m$alkyl,

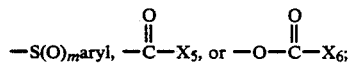

m is 0, 1 or 2;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl,

$X_5$ is hydroxy, alkoxy, aryloxy, amino, alkylamino or dialkylamino; and $X_6$ is alkyl, alkoxy or aryloxy; with the proviso that if $R_4$ is a 7-alkyl group, it must have a tertiary carbon atom bonded to the ring.

DETAILED DESCRIPTION OF THE INVENTION

Listed below are definitions of various terms used to describe this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino (-NH$_2$), alkylamino, dialkylamino, nitro, 4 carbon atoms), alkoxy (of 1 to 4 carbon atoms), alkanoyloxy, carbamoyl, or carboxyl groups.

The term "alkanoyl" refers to groups having the formula

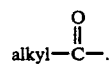

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethxy, etc.

The process of the present invention provides a more straightforward, economic method with increased yields for producing the resolved cis(+) enantiomers of formula I.

To carry out the present process, a racemic (mixture of the cis(+) and cis(−) enantiomers) compound of formula I is treated with an anhydride of the formula

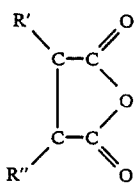
II wherein R' and R" are each hydrogen or R' and R" taken together can form a benzene ring which may be substituted with nitro or 1, 2, 3 or 4 halo substituents. A preferred compound of formula II is phthalic anhydride. This provides the racemic intermediate of the formula

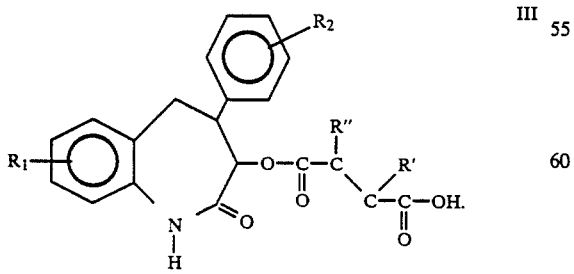
III

Treatment of compound III in a solvent, such as ethanol, with a resolving agent, such as optically active amines (with S-(−) alpha methyl benzylamine being preferred), provides a mixture of diastereomeric salts comprising the resolved crystalline salt

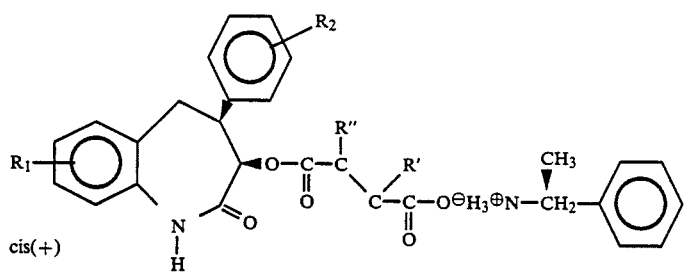
IV within the mother liquor which also contains the resolved predominantly cis(−) enantiomer derivatives of the formula

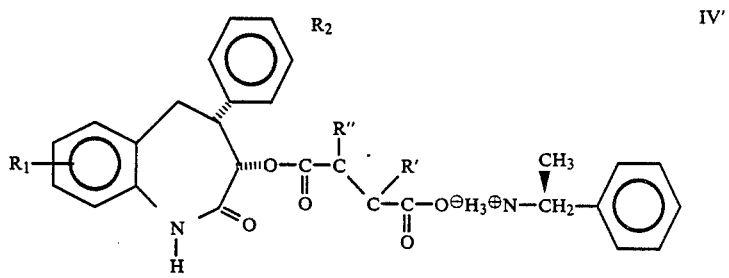
IV' in solution. Upon recovery of the crystalline salt IV, this cis(+) intermediate is thereafter treated with a base, such as lithium hydroxide, in the presence of solvents, e.g. methanol and water, to provide the desired cis(+) products of formula I as a crystalline solid and the resolving agent, e.g. (S-(−)-α-methyl benzylamine, in solution.

The improved process of the present invention additionally comprises methodology for recycling the cis(−) enantiomer derivative in the mother liquor, which is the by-product of the production of intermediate IV, to produce more of the desired products of formula I.

Thus, the present process further comprises treating the mother liquor containing the predominantly cis(−) form of compound IV' with a strong base, such as sodium hydroxide, in solvents, such as methanol and water, to isolate the resolved cis(−) enantiomer of formula

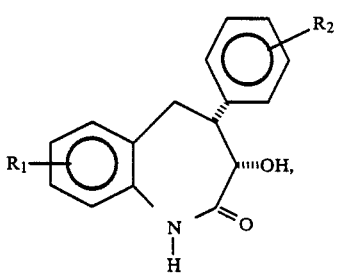
V as a crystalline solid, and the resolving agent in solution.

Compound V is thereafter oxidized by any convenient method, for example via treatment with oxalyl chloride and dimethyl sulfoxide in solvents, such as dimethylsulfoxide and methylene chloride, and in the presence of an organic base, e.g. triethylamine, to provide a compound of the formula

VI being a racemic product, because of the highly enolic nature of the ketone. Reduction of compound V with an agent, such as sodium borohydride, in the presence of a solvent, such as ethanol or isopropanol, provides the racemic (mixture of cis(+) and cis(−) enantiomers) compound of formula I. This so-formed mixture can thereafter be subjected to the methodology described above for compounds III and IV to provide the desired cis(+) enantiomeric products of formula I.

The intermediates of formula III, IV, IV', V and VI are novel compounds and as such are considered a part of the present invention.

The improved process of the present invention additionally comprises methodology for isolation and re-using the optically active amine resolving agent (e.g., S-(−)-α-methyl benzylamine).

Thus, the solutions containing this amine, obtained after the isolation of the cis-(+)-isomer formula I and cis-(−)-isomer formula V, are combined and after adjusting the pH to 12.0, can be extracted with an organic solvent, such as ether, ethyl acetate and the like, to obtain the resolving agent in the organic solvent. Finally, evaporation of the organic solvent followed by distillation of the residue provides the resolving agent, S-(−)-α-methyl benzylamine, thus completing the recycle.

To more fully understand the cooperation of the various parts of the novel process of the present invention, a flow chart, Scheme A, is provided below. Scheme A outlines, and shows the integral interaction of, the production of the resolved cis(+) compounds of formula I, the generation of additional racemic I starting material, and, the recycling of the resolving agent.

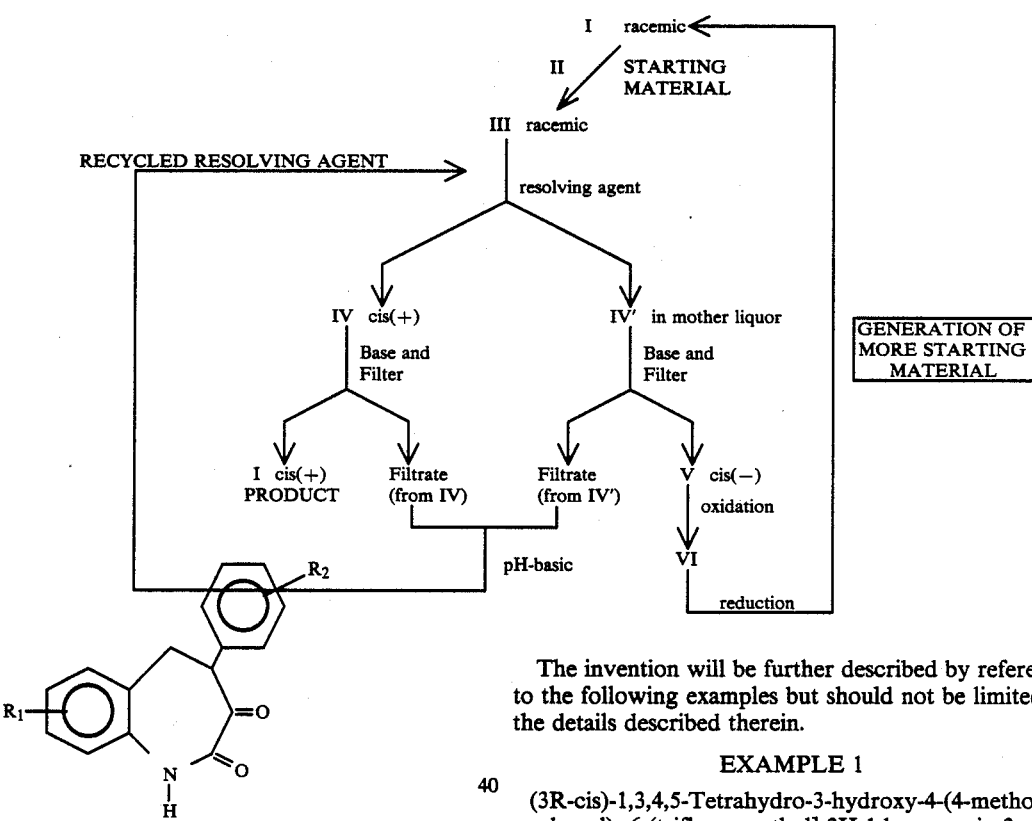

The invention will be further described by reference to the following examples but should not be limited to the details described therein.

EXAMPLE 1

(3R-cis)-1,3,4,5-Tetrahydro-3-hydroxy-4-(4-methoxyphenyl) -6-(trifluoromethyl)-2H-1-benzazepin-2-one A. (cis)-3-[(2-Carboxybenzoyl)oxy]-1,3,4,5-tetrahydro-4-(4-methoxyphenyl)-6-(trifluoromethyl) fluoromethyl)-2H-1-benzazepin-2-one Under argon, to dry methylene chloride (800 ml) and triethylamine (38 ml) was added DMAP (2.17 g) and (cis)-1,3,4,5-tetrahydro-3-hydroxy-4-(4- methoxyphenyl)-6-(trifluoromethyl)-2H-1-benzazepin2-one (62.51 g). After stirring, the so-formed suspension was cooled to about 15° C. and phthalic anhydride (39.53 g) was added. The resulting solution was warmed to room temperature and stirred for 4 hours. Upon quenching with 500 ml of dilute hydrochloric acid the layers were separated and the crystallized product from the methylene chloride layer was filtered and washed and dried in vacuo to give 84.8 g (95.4%) of the title A compound as a white crystalline solid, m.p. 161°–162° C.

B. (3R-cis)-3-[(2-Carboxybenzoyl)oxy]-1,3,4,5- tetrahydro-4-(4-methoxyphenyl)-6-trifluoromethyl) -2H-1-benzazepin-2-one, (S)-α-methylbenzenemethanamine (1:1) salt The title A compound (75.0 g) was dissolved in 1000 ml of 95% ethanol with stirring and heating. The ethanol solution was heated to reflux and S-(−)-α-methyl benzylamine (18.18 g) was added to the refluxing solution in one portion and stirred for 3 minutes. After removing the heat and discontinuing the stirring, the solution was seeded with authentic chiral salt and allowed to stand at room temperature overnight. The chiral salt was collected by filtration, then washed with cold (0° C.) ethanol (2×250 ml), and hexane (1×200 ml). The salt was dried n vacuo at 55° C. overnight to yield 37.8 g (41, theory 50) of the title B compound as a white crystalline solid. The mother liquor and ethanol washings were set aside for recycling.

C. (3R-cis)-1,3,4,5-Tetrahydro-3-hydroxy-4-(4-methoxyphenyl)-6-(trifluoromethyl)-2H-1- benzazepin-2-one To the title B compound (31.0 g) in methanol (25 ml) was added a solution of lithium hydroxide (8.28 g) in distilled water (250 ml). Mechanical stirring was started and the reaction solution was heated to 60° C. After heating for 10 minutes at 60° C. the clear solution became cloudy, and product began to precipitate from solution. Heating was continued for 45 minutes. The heating bath was removed, and the reaction mixture (white suspension) was diluted with 500 ml of water, and cooled to 0° C. with an ice bath. The precipitated solids were collected by filtration and washed with cold (0° C.) water (2×100 ml). The water washings were combined with the filtrate, and set aside. The solids were then washed with dilute hydrochloric acid (20 ml conc. HCl diluted to 200 ml, 1×200 ml) and hexane (200 ml). The solid was dried in vacuo at 60° C. overnight to obtain 16.5 g (94%) of crude product. The solid was dissolved in 250 ml of refluxing acetonitrile, then distilled until crystallization occurred. After allowing this mixture to stand at room temperature for 2 hours and then chilling at 0° C. overnight, the heavy crystals were collected by filtration and washed with 20% ethyl acetate in hexane (2×50 ml), then hexane (100 ml). The crystals were dried n vacuo at room temperature overnight to yield 14.9 g (85%) of the title compound, cis-(+)-isomer.

EXAMPLE 2

Recycling the cis(-) enantiomer cis(-)-1,3,4,5-Tetrahydro-3-hydroxy-4-(4-methoxyphenyl) -6-(trifluoromethyl) -2H-1-benzazepin-2-one A. (3S-cis)-1,3,4,5-Tetrahydro-3-hydroxy-4-methoxyphenyl)-6-trifluoromethyl)-2H-1-benzazepin-2-one The mother liquor and ethanol washings from Example 1, Part B, were evaporated to give a white solid, which was broken up and further dried for 4 hours under high vacuum at room temperature. This white solid was hydrolyzed and isolated using the procedure of Example 1, Part C but substituting sodium hydroxide for the lithium hydroxide. The solids obtained after filtration were dried in vacuo at 60° C. overnight to yield 23.93 g of the predominantly (about 5:1, (−) to (+)) cis(−) isomer, that is, the title A compound. The filtrate and washings were combined and set aside.

B. 4,5-Dihydro-4-(4-methoxyphenyl-6-(trifluoromehtyl) -1H-1-benzazepine-2,3-dione To methylene chloride (600 ml) was added oxalyl chloride (6.7 ml) under argon atmosphere. This solution was stirred and cooled to −78° C. While maintaining temperature and stirring, dimethylsulfoxide (20 ml) and more dry methylene chloride (200 ml) were added dropwise over 5 minutes. The title A compound (29.93 g) in dimethylsulfoxide (39 ml) and methylene chloride (200 ml) were added dropwise while maintaining the solution temperature below −70° C. After this addition the solution was stirred for 10 minutes. Maintaining −75° C., triethylamine (38.2 ml) was added and thereafter the reaction mixture was allowed to warm to room temperature and washed with two 100 ml portions of distilled water. Methanol (100 ml) was added to clarify the solution. The methylene chloride layer was washed with 100 ml of brine, separated, dried over magnesium sulfate, filtered and evaporated to give a yellow solid (24.71 g). This solid was crystallized from acetone to give the title B compound (18.26 g) as a yellow crystalline material, m.p. 221°-223° C.

C. (cis)-1,3,4,5-Tetrahydro-3-hydroxy-4-(4-methoxyphenyl)-6-(trifluoromethyl)-2H-1-benzazepin-2-one To the title B compound (20 g) in iospropyl alcohol (200 ml) was added portionwise sodium borohydride (8.48 g) with stirring and under argon, and the reaction was maintained at 25°-30° C. by periodic cooling with an ice bath. The reaction was monitored by TLC and appeared 90% complete after 45 minutes. The reaction was stirred at 25° C. for a total of 1.5 hours after which time TLC indicated the reaction was complete. The reaction was cooled to 0° C., and acetone (64 ml) was added portionwise with stirring to destroy the excess sodium borohydride. When the acetone addition was complete the reaction mixture was stirred an additional 30 minutes. Dilute hydrochloric acid (100 ml, 10 ml conc. HCl diluted to 100 ml) was added at 0° C. to pH-2. The reaction mixture was transferred to a 3 L RB flask and diluted with cold (0° C.) water (1600 ml) and stirred at 0° C. for 1 hour. The precipitated white solids were collected by filtration and washed with cold (0° C.) water (2×250 ml) and hexane (2×200 ml). The solid was dried in vacuo at 60° C. overnight to obtain 18.19 g (90%) of the title compound, m.p. 205°-208° C., which was a racemic mixture comprising the cis(+) and cis(−) isomers.

EXAMPLE 3

Recycling the Resolving Agent Isolation of S-(−)-α-methyl benzylamine

The water washings and the filtrate from Example 1, part C and Example 2, part A, were combined and the pH was adjusted to 12 by adding 30% NaOH solution. This was extracted with ether (3×300 ml) and the combined ether extract was washed with water, (1×100 ml) and brine (1×100 ml) and dried over anhydrous MgSO₄. Removal of ether followed by distillation of the residue gave 16.0 g of S-(−)-α-methyl benzylamine.

What is claimed is:

1. A process for preparing a resolved cis(+) enantiomer of a compound of the formula

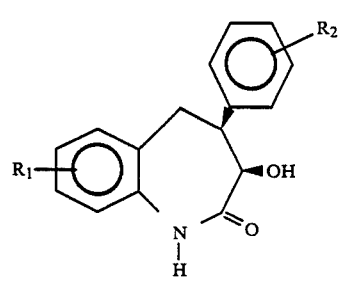

wherein R₁ and R₂ are each independently hydrogen, halogen, alkyl, alkoxy, aryloxy, arylalkoxy, diarylalkoxy, arylalkyl, cyano, hydroxy, alkanoyloxy,

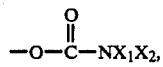

fluoro substituted alkoxy, fluoro substituted alkyl, (cycloalkyl)alkoxy, -NO$_2$, NX$_3$X$_4$, -S(O)$_m$alkyl,

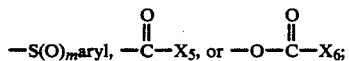

m is 0, 1 or 2;

X$_1$ and X$_2$ are each independently hydrogen, alkyl, aryl or heteroaryl, or X$_1$ and X$_2$ together with the nitrogen atom to which they are attached are pyrrolidinyl, piperidinyl or morpholinyl;

X$_3$ and X$_4$ are each independently hydrogen, alkyl, alkanoyl, arylcarbonyl, heteroarylcarbonyl, or

X$_5$ is hydroxy, alkoxy, aryloxy, amino, alkylamino or dialkylamino; and

X$_6$ is alkyl, alkoxy or aryloxy; with the proviso that if R$_4$ is a 7-alkyl group, it must have a tertiary carbon atom bonded to the ring, comprising the steps of:

(a) treating a racemic (mixture of the cis(+) and cis(−) enantiomers) compound of formula I with an anhydride of the formula

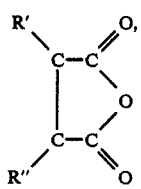

wherein R' and R" are each hydrogen or taken together with the carbons to which they are attached form a benzene ring which may be substituted with nitro or 1, 2, 3 or 4 halogens, to provide a racemic intermediate of the formula

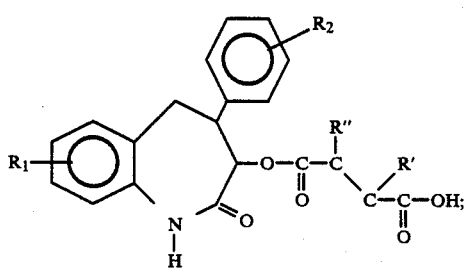

(b) treating a compound of formula III, in a solvent with a resolving agent, to provide a mixture of diasteromeric salts from which a compound of the formula

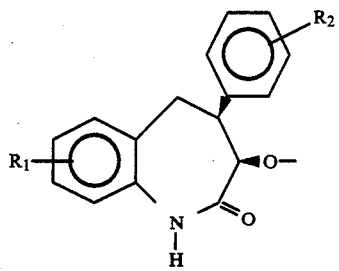

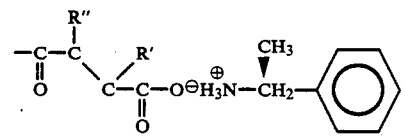

is crystallized; and (c) treating the compounds of formula IV with a base, in the presence of solvents, to provide the resolved cis(+) enantiomers of formula I.

2. The process of claim 1 wherein the anhydride of formula II is selected from phthalic anhydride, 3-nitrophthalic anhydride, tetrachlorophthalic anhydride and succinic anhydride.

3. The process of claim 1 wherein the solvents of steps (b) and (c) are selected from methanol, ethanol, acetonitrile and tetrahydrofuran.

4. The process of claim 1 wherein the base of step (c) is selected from LiOH, NaOH and KOH.

5. The process of claim 1 wherein said resolving agent is S-(−)-αmethyl benzylamine.

6. The process of claim 1 further comprising the steps of (d) isolating from the mother liquor of step (b), after the crystallized compound of formula IV has been separated out, the cis(−) enantiomer derivatives

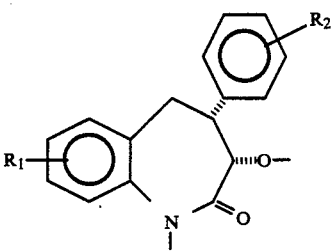

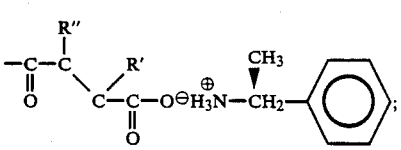

(e) hydrolyzing the so-formed derivatives of formula IV' with a base to provide

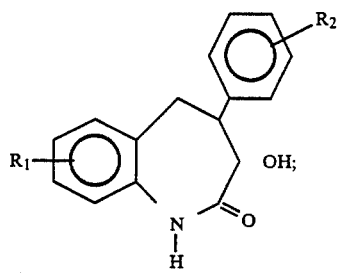

V (f) oxidizing the compounds of formula V to provide a racemic compound of the formula

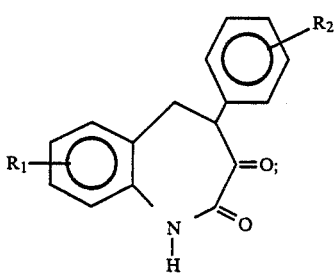

VI (g) reducing compounds of formula VI to provide a racemic (mixture of the cis(+) and cis(−) enantiomers) compound of formula I; and, (h) treating the so-formed racemic mixture of step (f) as in steps (a), (b) and (c) to provide additional resolved cis(+) enantiomer of formula I.

7. The process of claim 6 wherein the base of step (e) is selected from LiOH, NaOH and KOH.

8. The process of claim 6 wherein the oxidation in step (f) comprises treatment of compound V with an oxidizing reagent prepared from oxalyl chloride and dimethyl sulfoxide in solvents and in the presence of an organic base.

9. The process of claim 8 wherein said solvents are dimethylsulfoxide and methylene chloride.

10. The process of claim 8 wherein said organic base is triethylamine.

11. The process of claim 6 wherein the reduction in step (g) comprises treatment of compound VI with a reducing agent in the presence of a solvent.

12. The process of claim 11 wherein said agent is selected from sodium borohydride, lithium borohydride, lithium aluminum hydride and other similar hydride reducing agents.

13. The process of claim 11 wherein said solvent is selected from ethanol, methanol, isopropanol and tetrahydrofuran.

14. The process of claim 6 further comprising recycling of said resolving agent of step (b) by (i) combining the washings and filtrates from steps (c) and (e); and, (j) treating said combined washings and filtrate with a base to recover any excess resolving agent.

15. A compound of the formula

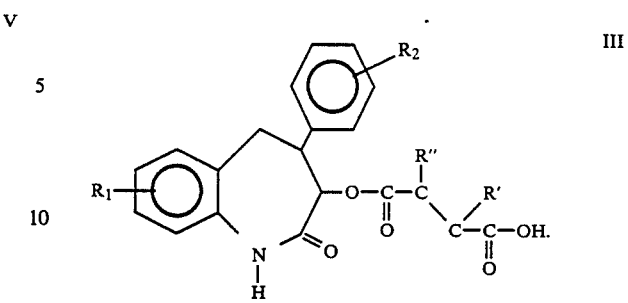

III wherein $R_1$, $R_2$, $R'$, $R''$, m, $X_1$, $X_2$, $X_3$, $X_4$, $X_5$ and $X_6$ are as defined in claim 1.

16. A resolved cis(+) enantiomer of the formula

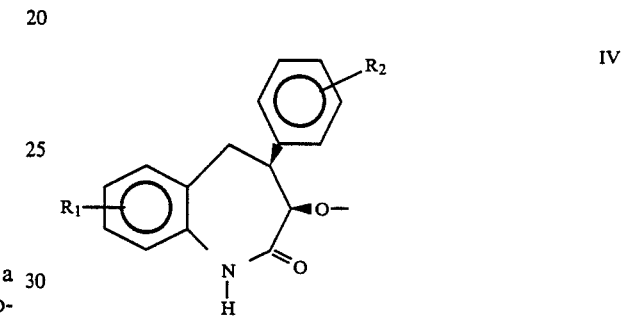

IV wherein $R_1$, $R_2$, $R'$, $R''$, m, $X_1$, $X_2$, $X_3$, $X_4$, $X_5$ and $X_6$ are as defined in claim 1.

17. A resolved cis(−) isomer of the formula

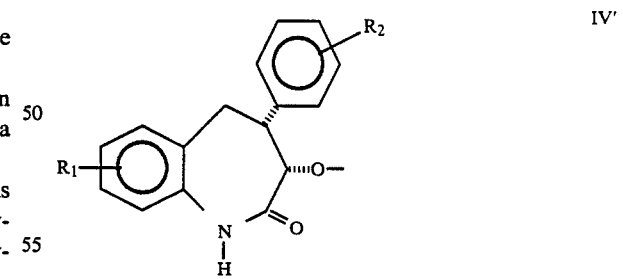

IV' wherein $R_1$, $R_2$, $R'$, $R''$, m, $X_1$, $X_2$, $X_3$, $X_4$, $X_5$ and $X_6$ are as defined in claim 1.

18. A compound of the formula

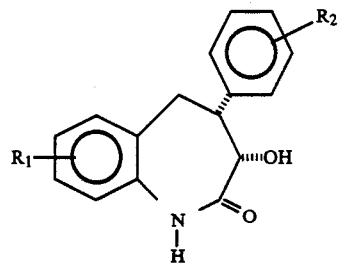
V
wherein $R_1$, $R_2$, R', R", m, $X_1$, $X_2$, $X_3$, $X_4$, $X_5$ and $X_6$ are as defined in claim 1.
19. A compound of the formula
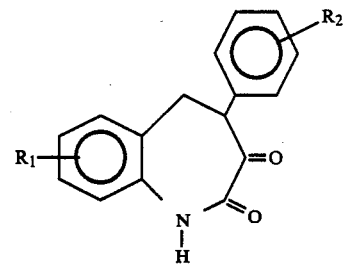
VI
wherein $R_1$, $R_2$, R', R", m, $X_1$, $X_2$, $X_3$, $X_4$, $X_5$ and $X_6$ are as defined in claim 1.
* * * * *